United States Patent
Harris et al.

(10) Patent No.: US 8,962,696 B2
(45) Date of Patent: *Feb. 24, 2015

(54) MICROEMULSION PREPARATION OF HIGH CONCENTRATION PROPOFOL FOR ANESTHETIC USES

(71) Applicants: Steven B. Harris, Rancho Cucamonga, CA (US); Nick J. Huang, Rancho Cucamonga, CA (US)

(72) Inventors: Steven B. Harris, Rancho Cucamonga, CA (US); Nick J. Huang, Rancho Cucamonga, CA (US)

(73) Assignee: Medos, Inc., Rancho Cucamonga, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/740,091

(22) Filed: Jan. 11, 2013

(65) Prior Publication Data

US 2013/0131186 A1    May 23, 2013

Related U.S. Application Data

(62) Division of application No. 10/588,424, filed as application No. PCT/US2005/004533 on Feb. 14, 2005, now Pat. No. 8,383,687.

(60) Provisional application No. 60/544,604, filed on Feb. 13, 2004.

(51) Int. Cl.
| | | |
|---|---|---|
| *A01N 31/08* | (2006.01) | |
| *A61K 9/107* | (2006.01) | |
| *A61K 9/00* | (2006.01) | |
| *A61K 31/05* | (2006.01) | |
| *A61K 47/10* | (2006.01) | |
| *A61K 47/14* | (2006.01) | |

(52) U.S. Cl.
CPC ............. *A61K 9/1075* (2013.01); *A61K 9/0019* (2013.01); *A61K 31/05* (2013.01); *A61K 47/10* (2013.01); *A61K 47/14* (2013.01); *Y10S 514/816* (2013.01)
USPC ............................ 514/731; 514/816; 424/643

(58) Field of Classification Search
CPC ..... A61K 9/0019; A61K 31/05; A61K 31/14; A61K 31/7016; A61K 47/44; A61K 47/12; A61K 47/14; A61K 47/24; A61K 47/26; A61K 47/10
See application file for complete search history.

(56) References Cited

U.S. PATENT DOCUMENTS

| | | | | |
|---|---|---|---|---|
| 6,726,919 B2 * | 4/2004 | Pace et al. | ...................... | 424/422 |
| 2004/0067919 A1 * | 4/2004 | Jee | ................................ | 514/171 |

FOREIGN PATENT DOCUMENTS

KR    1020010055736 A *  4/2001   ............ A61K 9/107

* cited by examiner

*Primary Examiner* — Lezah Roberts
*Assistant Examiner* — Nannette Holloman
(74) *Attorney, Agent, or Firm* — Jay P. Hendrickson

(57) ABSTRACT

The invention provides a method and a composition for enhancing the dissolution and bioavailable properties of propofol (2, 6 diisopropyl phenol) for use as an intravenously administered anesthetic in mammals. The method produces a self-microemulsifyable emulsion base composition that is utilized in the production of a water-based microemulsion preparation. In a preferred two (2) component base composition, the base composition consists of: a surfactant, containing polyethylene glycol; and liquid propofol. The microemulsion is prepared by mixing the base composition with a carrier liquid, which results in the formation of a microemulsion containing concentrations of propofol of up to about 4% by weight of propofol to the volume of the microemulsion. In a four (4) component base composition, the base composition consists of: a surfactant, containing polyethylene glycol; liquid propofol; a water-immiscible solvent; and ethanol. The microemulsion is prepared by mixing the base composition with a carrier liquid, which results in the formation of a microemulsion containing concentrations of propofol of up to about 10% by weight of propofol to the volume of the microemulsion.

21 Claims, No Drawings

MICROEMULSION PREPARATION OF HIGH CONCENTRATION PROPOFOL FOR ANESTHETIC USES

RELATED APPLICATIONS

This application is a divisional of application Ser. No. 10/588,424, which is the National Stage of International Application No. PCT/US2005/004533, filed Feb. 14, 2005, which claims the benefit of U.S. Provisional Application No. 60/544,604, filed Feb. 13, 2004.

FIELD OF THE INVENTION

The present invention relates to the preparation of physiologically isotonic oil-in-water type microemulsions of the anesthetic propofol to be used as a pharmaceutical for administration parenterally to mammals for the purpose of a general anesthesia.

BACKGROUND OF THE INVENTION

Systems for the water dispersion of drugs are necessary for intravenous administration of drugs that are not water soluble. Some of these systems use dispersions of hydrophobic liquids in water, also known as emulsions. Emulsions may be generally defined as somewhat uniformly-sized, stable or quasi-stable dispersions of liquid droplets in a second carrier liquid. Emulsions of microscopic size are often divided in the literature into nanoemulsions and microemulsions. Nanoemulsions cover the size range of 50-200 nm, and are kinetically stable systems with long term physical stability (against creaming or sedimentation, flocculation and coalescence). Because nanoemulsion systems are only kinetically but not thermodynamically stable, they must typically be created by energetic methods such as sonication and high pressure homogenization.

Emulsification systems in particular are needed for the administration of the anesthetic propofol (2, 6 diisopropyl phenol), a liquid which in is pure state is practically insoluble in water. Propofol is a well-known drug, which is relatively inexpensive to produce as a pure chemical, and which is presently used extensively in human and veterinary medicine as a general anesthetic agent. Propofol is capable of producing deep anesthesia, which resolves in a comparatively short time after administration of the drug is discontinued.

Presently, pharmaceutical propofol is prepared by dissolving it in soybean oil, then preparing an emulsion of this oil with egg phospholecithin in order to produce a final concentration of about 10% soybean oil in saline, with concentration of propofol standardized to 1% of the total liquid preparation. These emulsions, which have the appearance of milk, have droplet sizes of up to 200 nm and may be referred to as "nanoemulsions." Such commercial propofol emulsions, despite addition of preservatives, are similar to intravenous lipid nutritional preparations, and are excellent preservative media for viruses or even growth media for bacteria. For this reason, all propofol preparations in the United States are restricted to single-patient-use vials and ampoules, with directions for discarding of penetrated containers within hours after first use.

To be distinguished from nanoemulsions are microemulsions, a type of emulsion with a particularly small droplet size, usually ranging from less than about 5 to 50 nm in diameter. Microemulsions are characteristically optically transparent due to the small light scattering from very small droplets, giving them a visual appearance similar to true solutions. Microemulsions are also typically thermodynamically stable with respect to instability, and they often therefore form spontaneously, if given sufficient time. For present purposes, the most desirable microemulsions assemble spontaneously when certain hydrophobic chemicals and water are mixed by simply stirring the mixture, without the need for vigorous agitation, such as sonication.

In this regard, there is particular need for the development of propofol microemulsions for pharmaceutical intravenous use that are optically clear, enabling the use of light diffraction to detect the presence of potential contamination from foreign elements such as bacteria, which scatter light. Also, there is need for propofol preparations which are not as conducive to growth of bacteria and fungi, as the present oil and phospholecithin preparations are. There is a need for propofol preparations which have a long shelf life, and which are easily sterilized. Finally, there is a need for propofol preparations containing far more than the 1% concentration presently commercially available, for use in larger animals, such as horses. Presently such animals requiring general anesthesia must frequently be transported from the field to an urban anesthesia suit setting for gas anesthesia, a procedure which is difficult and expensive. An inexpensive high concentration propofol preparation which could be taken to the animal in the field might serve the general anesthetic needs of a significant fraction of these animals.

Generally, current commercially available emulsion systems for the intravenous delivery of propofol utilize ordinary opaque nanoemulsions of the oil-in-water type. Recently, however, a general microemulsion system for pharmaceutical delivery of active compounds has been disclosed in U.S. Pat. No. 6,602,511, which generally describes a complex formulation for a microemulsion containing: water and a component for adjusting polarity, a "surfactant film modifier" (e.g. ethanol), a pharmaceutically acceptable oil (most preferably "a triglyceride containing at least 70% of fatty acids having 8-10 carbon atoms"), and a mixture of a hydrophilic and hydrophobic surfactant up to about 15% by weight of the total emulsion. The '511 patent claims that the formulation can be used to emulsify a broad range of active compounds such as a "proton pump inhibitor, calcium channel blocker, beta blocker, anesthetic, steroid, antioxidant, rennin inhibitor, alkaloid, cytostatica, anti-coagulant, lipid regulating agent, anti-depressant, neuroleptic, immunosuppressant, immunomodulator, antibiotic, [and] anti-inflammatory agent". Unfortunately, the patent discloses the application of its microemulsion formulation to only two active compounds: felodipine and "indeno indole". The usefulness of the invention as a microemulsion containing an anesthetic such as propofol is not disclosed. In this regard, it is noted that patent states that the invention produces a microemulsion which is "transparent and slightly viscous one phase liquid", but the patent is silent as to the transparency of the microemulsion after the addition of either felodipine or indeno indole. The present inventors note, however, that in order to adapt the complex formulation of the patent to intravenous use, it would be necessary to add a significant amount of carrier liquid and that doing so would cause a significant degradation in the transparency of the microemulsion. The patent also discloses the need for a two (2) component surfactant system: a hydrophilic and a hydrophobic surfactant, which further adds to the complexity of the formulation. Here, the '511 patent follows the common belief that microemulsions systems are most easily made by use of a "co-surfactant" to decrease droplet interfacial tension. However, the inclusion of a hydrophobic surfactant actually retards the formation of the desired microemulsion in water, and is completely unnecessary if the hydrophobic surfactant is chosen properly.

As a result, what is needed is a simple propofol composition for the production of high concentrations of propofol in a completely transparent microemulsion that can be used as an intravenously administered anesthetic, and if necessary can be suitably colored in order to identify different concentrations of propofol in different preparations. In addition, there is needed a propofol self-microemulsifiable base composition which uses only a single hydrophillic surfactant, is easy to sterilize, can be stored indefinitely until the anesthetic is needed, after which it can easily be reconstituted by addition of a physiologic saline or similar water-based carrier. The present invention satisfies these needs, among others.

SUMMARY OF THE INVENTION

The present invention generally provides a novel method and a composition for enhancing the dissolution and bioavailable properties of propofol (2, 6 diisopropyl phenol) for use as an intravenously administered anesthetic in mammals. The method of the present invention produces a self-microemulsifiable emulsion base composition that is utilized in the production of a water-based microemulsion preparation for use as an anesthetic. In a preferred two (2) component base composition, the base composition consists of: a surfactant, containing polyethylene glycol; and liquid propofol. The microemulsion is prepared by mixing the base composition with a carrier liquid, which results in the formation of a microemulsion containing concentrations of propofol of up to about 4% by weight of propofol to the volume of the microemulsion. In a four (4) component base composition, the base composition consists of: a surfactant, containing polyethylene glycol; liquid propofol; a water-immiscible solvent; and ethanol. The microemulsion is prepared by mixing the base composition with a carrier liquid, which results in the formation of a microemulsion containing concentrations of propofol of up to about 10% by weight of propofol to the volume of the microemulsion. The present invention produces a base composition that is a self-microemulsifiable, anhydrous, homogenous, and optically transparent liquid that can be stored for later use almost indefinitely. As a result, the preparation of the propofol microemulsion by mixing the base composition with the carrier liquid can be delayed until the anesthetic is needed in the laboratory, clinic or hospital. Further, the present invention produces a microemulsion which is thermodynamically stable and is also optically transparent. The transparency of the microemulsion permits the anesthetic to be tinted with different colors in order to distinguish different propofol concentrations, so that accidents involving anesthetics of similar appearance, but containing different concentrations of propofol, are more easily avoided. The transparency of the microemulsion also makes it easier to detect whether the anesthetic has been contaminated. The microemulsion of the present invention is also easily sterilized by simply heating the surfactant before it is mixed with the liquid propofol and by using a sterilized carrier liquid. The characteristics of the invention are also extremely conducive to cold filtration filter sterilization.

DETAILED DESCRIPTION OF THE INVENTION

The present invention generally provides a novel method and a composition for enhancing the dissolution and bioavailable properties of propofol (2, 6 diisopropyl phenol) for use as an intravenously administered anesthetic in mammals. The method of the present invention produces a self-microemulsifiable emulsion base composition that is utilized in the production of a water-based microemulsion preparation for use as an anesthetic. In a preferred two (2) component base composition, the microemulsion preparation contains concentrations of propofol of up to about 4% by weight of propofol to the volume of the microemulsion, and in a four (4) component base composition, the microemulsion preparation contains concentrations of propofol of up to about 10% by weight of propofol to the volume of the microemulsion.

The preferred two (2) component base composition consists essentially of: a non-ionic surfactant, containing polyethylene glycol (hereinafter referred to as a "PEG-containing surfactant"; and a propofol solution, containing liquid propofol which has been mixed with 1% vitamin E (free alpha tocopherol) in order to prevent oxidation (hereinafter referred to simply as "propofol" or "liquid propofol"), in which the relative concentration of surfactant to propofol included in the base composition is about eight (8) parts or more surfactant to about one (1) part propofol.

The preferred method of producing the self-microemulsifiable emulsion base composition consists essentially of mixing a predetermined amount of the PEG-containing surfactant, preferably heated to a preparation temperature above its melting point, with a predetermined amount of the liquid propofol. The mixing is performed by simply stirring or agitating the components for a few minutes or less until the solution becomes transparent. The resulting base composition is a self-microemulsifiable, anhydrous, homogenous, and optically transparent liquid, with low viscosity at the preparation temperature. The water-based microemulsion is then prepared by mixing the base composition with a predetermined amount of a carrier liquid, which contains water and is isotonic to blood, such as 0.9% saline, 5% dextrose, or other isotonic solutions containing a crystalloid or a colloid which are intended for peripheral intravenous administration. Again, the mixing is performed by simply stirring or agitating the components for a few minutes or less until the solution becomes transparent. The resulting microemulsion preparation may contain concentrations of propofol of up to about 4% by weight of the propofol to the volume of the microemulsion (w/v), and still exhibit all of the characteristics of a microemulsion. The microemulsion is thermodynamically stable at room temperature and is optically transparent, but has a pale yellow color due to the inclusion of propofol. Examples #1 and #2 at the end of this section set forth specific examples of the preparation of a two (2) component base composition and then using the base to prepare a microemulsion containing concentrations of propofol of 1% (w/v) and 4% (w/v), respectively. Example #3 sets forth the results of the intravenous administration of the microemulsion containing a concentration of propofol of 4%, prepared as in Example #2, to a canine, without any evidence of pain upon intravenous injection to the conscious animal.

Although the preferred method of producing the two (2) component base composition heats the surfactant to a preparation temperature above its melting point, the base may also be prepared at lower preparation temperatures. The lower preparation temperatures merely require that the liquid preparation of surfactant and liquid propofol must be stirred or agitated for a longer period of time. In addition to heating the solution, it can also be prepared by sonication or by using any mixing method that creates a homogeneous liquid.

The ability of the present invention to produce water-based microemulsion preparations containing concentrations of propofol of up to 4% by weight of propofol to the volume of the microemulsion, is a significant improvement over existing oil-in-water preparations that are only capable of producing propofol concentrations of up to about 1% by weight of propofol to the volume of the preparation. The present invention also constitutes a significant improvement over other attempts to produce an injectable microemulsion containing higher concentrations of propofol. For example, U.S. Pat. No. 6,602,511 (hereinafter the '511 patent) discloses a complex formulation for a microemulsion containing: water (not the major component), a component for adjusting polarity, a "surfactant film modifier" (e.g. ethanol), a pharmaceutically acceptable oil (most preferably "a triglyceride containing at least 70% of fatty acids having 8-10 carbon atoms"), and a mixture of a hydrophilic and hydrophobic surfactant up to about 15% by weight of the total emulsion. The '511 patent claims that the formulation can be used to emulsify a broad range of active compounds such as a "proton pump inhibitor, calcium channel blocker, beta blocker, anesthetic, steroid, antioxidant, rennin inhibitor, alkaloid, cytostatica, anti-coagulant, lipid regulating agent, anti-depressant, neuroleptic, immunosuppressant, immunomodulator, antibiotic, [and] anti-inflammatory agent". Unfortunately, the patent discloses the application of its microemulsion formulation to only two active compounds: felodipine and "indeno indole". The usefulness of the invention as a microemulsion containing an anesthetic such as propofol is not disclosed. In this regard, it is noted that patent states that the invention produces a microemulsion which is a "transparent and slightly viscous one phase liquid", but the patent is silent as to the transparency of the microemulsion after the addition of either felodipine or indeno indole, or after the addition of further water to this water-in-oil preparation. The present inventors note, however, that in order to adapt the '511 formulation to intravenous use, it would be necessary to add a significant amount of carrier liquid. Since the microemulsions disclosed in the '511 patent are bicontinuous type microemulsions or water-in-oil microemulsions in which a major component (about 44 to 61%) is oil and a minor component (15%) is surfactant, it is apparent that adding the water-based liquid necessary for intravenous use would cause a significant degradation in the transparency of the emulsion—i.e. when converted from water-in-oil to an oil-in-water preparation, these preparations would no longer be microemulsions. In contrast, the present invention contains sufficient surfactant to produce true oil-in-water microemulsions, containing concentrations of propofol of up to 4% of the microemulsion, which is completely transparent, and capable of being further diluted by water without any disruption of the microemulsion system.

There are other advantages of the present invention over the '511 patent, not the least of which is that the present invention is capable of producing an intravenously injectable microemulsion containing a high concentration of propofol by using a very simple system of only a single type of PEG-containing surfactant and a carrier liquid such as saline. The '511 patent, on the other hand, requires the use of up to six (6) or more chemicals in order to ostensibly produce a water-in-oil type microemulsion for pharmaceutical use. Other disadvantages of using some of the components of the 511 patent include greater potential for bacterial growth, due to the fact that some of the preferred components, such as soybean phospholecithins, are sources of both phosphorus and nitrogen. In contrast, the present invention discloses mixtures which contain only carbon, oxygen, and hydrogen in addition to sodium chloride. In addition the 2-component base preparations of the present invention present compositions which contain no oil and the 4-component base compositions may be packaged so as to contain no water.

The propofol microemulsion of the present invention has several advantages and features as an intravenously injectable anesthetic preparation that is not possible with current propofol formulations. For example, the ability of the present invention to produce an anesthetic liquid which is optically clear, allows the anesthetic to be tinted with different colors in order to distinguish different propofol concentrations, so that accidents involving solutions of similar appearance, but containing different propofol concentrations, are more easily avoided. In this regard, the present inventors have successfully used intravenous compatible preparations of fluorescein dye (yellow) and methylene blue dye (blue) to color various anesthetic solutions prepared in accordance with the method of the present invention. It will be apparent to those skilled in the art that other medical compatible dyes can be used to produce other colors, such as the potential use of vitamin B12 to produce a primary red color.

Another advantage of the present invention is that, due to the anesthetic liquid's property of being optically transparent, it is much easier to detect the presence of any bacterial and fungal contamination by examination, because living cells, as well as many gross contaminants, scatter light. In this regard, current anesthetic preparations containing oil and phospholecithin are particularly susceptible to contamination from the growth of bacteria and fungus; however, the anesthetic solution of the present invention is much less likely to become contaminated because it does not require the use of triglyceride oil, or of nitrogen or phosphorus containing surfactants.

Additionally, the microemulsion preparation of the present invention is easily sterilized. For example, the surfactant Solutol® is sterilized when it is heated until reaching about 121° C., then cooled to about 50° C., and liquid propofol may be filter- sterilized and then added to the molten Solutol®, thereby creating a sterile base composition. This composition may in turn be easily filter-sterilized if necessary by passing the liquid through a 0.2 micrometer filter. This base may be commercially packaged in sterile mixing vials. Mixing the sterilized base composition with sterilized saline creates a sterilized microemulsion liquid preparation. Further sterilization of the final microemulsion may also be performed, if desired, by passing the microemulsion through a 0.2 micrometer filter. Propofol microemulsions of the present invention pass such filters much more easily than do current oil-in-water nanoemulsions, such as soybean emulsions that pass bacterial filtration only with some difficulty, due to their larger droplet size.

Another feature of the present invention is that the self-microemulsifiable emulsion base composition may be stored in an air tight vial, ampoule, or other similar container almost indefinitely. As a result, the preparation of the propofol microemulsion, by mixing the base composition with a carrier liquid, can be delayed until the aesthetic is needed in the laboratory, clinic or hospital. Although the preferred base composition will solidify after it cools to room temperature, the base can be easily returned to its liquid state by warming the base to a temperature of approximately 45° C. Then the microemulsion liquid preparation is readily formed by mixing the liquid base with the carrier liquid. This feature greatly enhances the usefulness and convenience of microemulsions prepared in accordance with the method of the present invention. Current oil-in-water type microemulsions containing the anesthetic propofol cannot be prepared in similar fashion because they are not thermodynamically stable, and require technologically sophisticated emulsification preparation, analogous to homogenization of milk. This cannot be done in the field or at the bedside.

The self-microemulsifiable emulsion base composition of the present invention includes a PEG-containing surfactant that is completely miscible with water, meaning that the PEG-containing surfactant has a high affinity for water and readily dissolves in water, where the surfactant forms an optically clear so-called "micellar solution" (i.e., not a true chemical solution, but rather an apparent solution in which the surfactant actually consists of aggregates, which are essentially microemulsion particles which lack chemically distinct cores). In a less polar solvent such as ethanol, these classes of surfactants do form true chemical solutions. It is this characteristic of forming a spontaneous micellar solution in water that causes the solubilized composition of propofol and this class of surfactant to form a micellar microemulsion in the water-based carrier liquid.

Generally, the inventors have discovered that co-surfactants are not required for formation of microemulsions, so long as certain PEG-containing surfactants are used. PEG-containing surfactant molecules that form acceptable propofol microemulsions in the water-based carrier liquid are characterized by surfactant molecules in which the total length of the polyethylene glycol portion of each surfactant molecule, whether linear or non-linear, is from 2 to 6 times longer than the length of the hydrophobic hydrocarbon portion of the molecule. A decrease in this ratio to below 2 typically does not produce surfactants that form micellar solutions in water, nor do the surfactants form propofol microemulsions, although such surfactants may form ordinary nanoemulsions. A value above 6 in the ratio of the length of the polyethylene glycol portion to the hydrophobic portion of the surfactant molecule will allow both micellar solutions and microemulsions to form, but will also increase the viscosity and melting point of the surfactant, substantially increasing the time needed to prepare the base composition. This higher ratio will also reduce the loading factor of the surfactant, which is defined as the amount of propofol that a given weight of surfactant is able to solubilize into water in order to form an optically clear microemulsion.

The most acceptable PEG-containing surfactants for use as propofol solubilizers share some common features: 1) they are non-ionic and depend on PEG (polyethoxy) components for their high affinity for and solubility in water; 2) the hydrophobic R group(s) of the surfactant must be bio-compatible and have a melting point close to or below body temperature, and 3) the PEG chain or chains attached to one end of the R group(s) must be long enough in total length to limit the size of surfactant micellar aggregates in water, which happens due to the increasing PEG/water interaction. This last feature ensures that the smallest type of micellar aggregates (or optically clear microemulsions which resemble micellar aggregates in scale) that form in water are thermodynamically stable. Typically, the cloud point concentration of the preferred pure surfactants in water is very high or nonexistent.

More specifically, the most preferred PEG-containing surfactant for use in the preparation of the base composition of the present invention can be defined as belonging to one of two classes. A first class of PEG-containing surfactant has the general structure of [POE(n)]subm-R'-R; where POE is a polyoxyethylene moiety (also known as a polyethylene glycol or PEG moiety) of -mer number n, and having m of these POE functional groups attached to R'; where the value of m is one to three; where R' is a linking moiety, particularly glyceryl, sorbitan, ester, amino, or ether (oxygen) functions; and where R is a hydrophobic moiety consisting of saturated or unsaturated alkyl or alkylphenyl groups. Examples of non-ionic surfactants within this first class are polyoxyethylene monoalkyl ethers, polyoxyethylene alkylphenols, polyethylene glycol fatty acid monoesters, polyethylene glycol glycerol fatty acid esters, polyoxyethylene sorbitan fatty acid esters, and polyoxyethylene sterols. Mixtures of any of these chemical moieties also function as good surfactants for the purposes of the invention.

A useful and preferred subclass within the first class of PEG-containing surfactants includes surfactants having a structure further defined by a ratio of A, which is the total number of POE -mer units in the surfactant (given by the product of -mer number n and total PEG chain number m per molecule), to B, which is the number of carbons in the hydrophobic functional group R, is between about 0.7 and 4; preferably with A/B being in the range from about 1 to 2. Examples of non-ionic surfactants within this subclass are PEG-15 monolaurate, PEG-20 monolaurate, PEG-32 monolaurate, PEG-48 monolaurate, PEG-13 monooleate, PEG-15 monooleate, PEG-20 monooleate, PEG-32 monooleate, PEG-72 monooleate, PEG-15 monostearate, PEG-660 12-hydroxystearate (BASF Corporation "Solutol®"), PEG-23 monostearate, PEG-40 monostearate, PEG-72 monostearate, PEG-20 glyceryl laurate, PEG-30 glyceryl laurate, PEG-20 glyceryl stearate, PEG-20 glyceryl oleate, PEG-30 glyceryl monooleate, PEG-30 glyceryl monolaurate, PEG-40 glyceryl monolaurate, PEG-20 sorbitan monooleate (polysorbate 80, Tween 80), PEG-20 sorbitan monolaurate (Tween 20), PEG-20 sorbitan monopalmitate (Tween 40), and PEG 20 sorbitan stearate (Tween 60), PEG-40 sorbitan monooleate, PEG-80 sorbitan monolaurate, POE-23 lauryl ether, POE-20 oleyl ether, PEG 30-60 nonyl phenol series (Triton N series), PEG 30-55 octyl phenol series (Triton X series, particularly X-305 (POE 30) and X-405 (POE 40). Mixtures of any of these surfactants also function well.

A second class of PEG-containing surfactants is derived from triglyceride oils, and has the general structure of [R'-(POE)subn]sub3-glyceride, where POE is a polyoxyethylene moiety (also known as a polyethylene glycol or PEG moiety) of -mer number n, inserted between fatty acid acyl residues R' and a glycerol residue (glyceride), which had, before polyethoxylation, been attached directly to the acyl residues as a common triglyceride. Examples of non-ionic surfactants within this second class are the polyoxyethylated vegetable oils, such as polyethoxylated corn oil or polyethoxylated castor oil. Mixtures of these polyoxyethylated vegetable oils also function as good surfactants for the purposes of the invention.

A preferred subclass within the second class of PEG-containing surfactants includes surfactants having a structure further defined by a ratio of A, which is the total number of POE -mer units in the surfactant (given by the product of -mer number n and total PEG chain number 3 per molecule), to B, which is the number of carbons in the 3 fatty acid R' residues is between about 0.5 and 3; preferably with A/B being in the range from about 0.6 to 1.5. Examples of non-ionic surfactants within this subclass are PEG-40 palm kernel oil, PEG-50 hydrogenated castor oil, PEG-40 castor oil, PEG-35 castor oil (e.g., Cremaphor®-35), PEG-60 castor oil, PEG-40 hydrogenated castor oil, PEG-60 hydrogenated castor oil, and PEG-60 corn oil. Mixtures of these surfactants also function well for purposes of the invention.

A third class of PEG-containing surfactants, analogous to the two above, can in theory be manufactured by polyethoxylation of diester compounds consisting of fatty acid esters of biocompatible dialcohols, such as propylene glycol. The inventors expect that these compounds will have properties substantially the same as those described in the first two classes of PEG-containing surfactants, so long as the ratio of residue R fatty acid carbons to PEG mer-number is maintained between 0.5 to 4.

Finally, it is noted that mixtures of the two chemically defined classes of PEG-containing surfactants also function well in the present invention. All of the preferred PEG-containing surfactants are compatible and function well when used as mixtures, but it is a feature of the invention that particular mixtures are not needed or preferred, and preferred surfactants have been chosen to work as single agents in production of microemulsions. This is in contrast to prior inventions which specify certain surfactant mixtures aimed at attaining particular "HLB" (hydrophobic lipophilic balance) ratios for a mixture of 2 or more surfactant types.

Adding a PEG-containing surfactant, such as PEG-660 12 hydroxystearate (BASF Corporation's Solutol®) to water causes formation of a "micellar solution" of self-aggregated surfactant clusters of diameter of about 12 nm. The solution forms an optically clear dispersion analogous to a microemulsion, but technically not a microemulsion because the homogenous liquid contains only one component other than water. With the addition of a hydrophobic guest solute, like propofol, such micellar solutions are generally described as "microemulsions". It is questionable, however, whether the molecular structure of such aggregates is always that of the classical two-component lipid-in-water emulsion, containing a tiny droplet of hydrophobic substance "coated" with surfactant. Doppler light scattering studies done by the inventors show that the microemulsions formed from all classes of surfactants described in the present invention have diameters as small as 12 nm (120 Angstroms), meaning the particle radius is just less than the length of a single uncoiled surfactant molecule (about 7 nm). Such small and simple structures have no room for a classical emulsion hydrophobic liquid drop core, but must contain their embedded solvents and hydrophobic guest molecules (like propofol) in a relatively jumbled core, closely interwoven by the hydrophobic heads of the surfactant ensemble, which are interlocking and probably touching from opposite sides of the micelle.

Depending upon the specific PEG-containing surfactant selected for use in preparing the microemulsion liquid preparation, propofol concentrations of up to about 4% by weight of propofol to the volume of the microemulsion preparation are attainable. In this regard, however, due to the relatively low viscosity of Solutol®, it is a most preferred PEG-containing surfactant in that the utilization of Solutol® produces a microemulsion having the highest concentration of propofol of about 4%. Again, the microemulsion preparation is transparent.

In the four (4) component base composition of the present invention, water-based microemulsion preparations containing concentrations of propofol of up to about 10% by weight of propofol to the volume of the microemulsion are attainable by including a water-immiscible solvent and ethanol in the base composition. In this embodiment, the base composition consists essentially of: a PEG-containing surfactant; liquid propofol; a water-immiscible solvent; and ethanol, in which the relative concentration of surfactant to propofol included in the base composition is not less than about three (3) parts, and preferably about three (3) to five (5) parts surfactant to about one (1) part propofol, the relative concentration of water-immiscible solvent to propofol is about three to five (3) to five (5) parts solvent to about ten (10) parts propofol, and the relative concentration of ethanol to propofol is about five (5) to six (6) parts ethanol to about ten (10) parts propofol.

In this embodiment the preferred method of producing the self-microemulsifiable emulsion base composition consists essentially of mixing in any order a predetermined amount of the PEG-containing surfactant, preferably heated to a preparation temperature above its melting point, with predetermined amounts of the liquid propofol, water-immiscible solvent, and ethanol as a co-solvent. The mixing is performed by simply stirring or agitating the components for a few minutes or less until the solution becomes transparent. The resulting base composition is a self-microemulsifiable, anhydrous, homogenous, and optically transparent liquid, with low viscosity at the preparation temperature. The water-basedm microemulsion is then prepared at room temperature by mixing the base composition with a predetermined amount of carrier liquid, which contains water and is isotonic to blood, such as 0.9% saline, 5% dextrose, or other isotonic solutions containing a crystalloid or a colloid which are intended for intravenous administration. Again, the mixing is performed by simply stirring or agitating the components for a few minutes or less until the solution becomes transparent. The resulting microemulsion preparation can contain concentrations of propofol of up to about 10% by weight of the propofol to the volume of the preparation and still exhibit the characteristics of a microemulsion. The microemulsion is thermodynamically stable at room temperature and is optically transparent, but has a pale yellow color due to the inclusion of propofol. Examples #4, #6, and #7 at the end of this section set forth specific examples of this embodiment in the preparation of a self-microemulsifiable emulsion base composition and then using the base to prepare a microemulsion containing concentrations of propofol of about 1% (w/v) and up to about 10% (w/v). Example #5 sets forth the results of the administration of a microemulsion containing a concentration of propofol of 10%, prepared as in Example #4, to a canine. Example #8 sets forth the results of the administration of a microemulsion containing a concentration of propofol of 1%, prepared as in Example #7, to a canine.

This formulation of the present invention also exhibits substantial advantages over other attempts to solubilize propofol for use as an anesthetic. Clearly, the ability of this embodiment to produce propofol concentrations in a microemulsion of up to 10% by weight of the microemulsion is a further substantial improvement over oil-in-water type preparations. And, comparing this embodiment of the present invention to the formulation disclosed in the '511 patent reveals that the present invention is, once again, seen to be a significant improvement over the formulation described in the '511 patent. In addition to the fact that this embodiment of the present produces a microemulsion that is transparent at all concentrations of water and, therefore, superior to the '511 water-in-oil formulation, this embodiment also contains fewer components than the components described in the '511 patent in that this embodiment does not contain a hydrophobic surfactant.

This embodiment of the present invention also exhibits all of the advantages and features of the preferred embodiment and exhibits at least two further advantages. One obvious advantage is that even higher concentrations of propofol are attainable, making the anesthetic useful in large mammals (for example, a 500 kg horse requires about 1.5 grams of propofol for induction of general anesthesia, which is 75 mL of 5% microemulsion, but 375 mL of 1% emulsion). Another advantage relates to the ability of being able to delay the mixture of the base composition with the carrier liquid. In the preferred embodiment, it was pointed out that the base composition could be added to the carrier liquid at any time after the base was prepared, but that the base needed to be re-warmed before doing so. In this embodiment there is no need to re-warm the base, because it does not solidify at room temperature, rather it remains as a thermodynamically stable and transparent liquid. As a result, the base prepared in accordance with this formulation can be stored indefinitely, and sometime later shipped to a laboratory, clinic or hospital where it can be added directly to a carrier liquid in order to form the intravenously injectable microemulsion. A specific example of the ability to use a base composition that has been prepared in accordance with this embodiment is set forth in Example #9.

Acceptable water-immiscible biocompatible solvents for use in the present invention must be biocompatible and non-toxic to mammals and generally can be selected from one of three (3) groups of esters: monoesters, diesters, and triesters. The esters are formed from a group of liquids composed of aliphatic (saturated and unsaturated; straight and branched chain) acid or alcohol residues. The monoesters are composed of residues from mono-alcohols and mono-acids. The diesters are composed of residues from mono-acids and di-alcohols, or from di-acids and mono-alcohols. The triesters are composed from mono-acids and tri-alcohols, or from tri-acids and mono-alcohols.

For the monoesters, the preferred saturated or unsaturated aliphatic acid residues are selected from the group containing acetic, propionic acid, or other saturated or unsaturated biocompatible aliphatic acids. Fatty acids with an even number of carbons of length Csub8 or longer are preferred, due to unpleasant taste and odor of short chain fatty acids and ester preparations which contain them. The saturated or unsaturated aliphatic alcohol residue for the ester is preferably selected from the group containing ethyl, n-propyl alcohol, or other saturated or unsaturated biocompatible aliphatic alcohols. Many such alcohols are straight-chain mono-alcohols of eight or more carbons, such as n-octanol. Alkyl alcohols with an even number of carbons are preferred. Preferred examples of monoester solvents are ethyl oleate, propylene glycol dicaprylate, isopropyl myristate, ethyl laurate, butyl oleate, oleyl acetate, oleyl propionate, octyl octanoate, octyl decanonate, and oleyl oleate.

Preferred diesters are also selected due to biocompatibility of the alcohols and carboxylic acids derived from the ester residues, as well as choice of residues to formulate an ester which is liquid at near body temperature. Each residue will preferably correspond to a carboxylic acid or alcohol which is biocompatible. A diester may be composed of two carboxylic acid residues condensed with one di-hydroxy alcohol, or one di-carboxylic acid residue with two mono-alcohols.

For diesters derived from di-alcohols and mono-acids, the preferred di-alcohol is selected from the group of biocompatible small di-hydroxy alcohols, such as propylene glycol, 1,2 butanediol, and 1,3 butanediol. The preferred aliphatic mono-acids are selected from the group which contains acetic or propionic acid, or the aliphatic acids which are fatty acids with an even number of carbons of length Csub8 or longer. Preferred examples of such liquid diesters based on di-alcohols and mono-acids are propylene glycol dilaurate, propylene glycol dioleate, propylene glycol dicaprylate, and 1,2 butane glycol dioleate.

For diesters derived from di-acids and mono-alcohols, the di-acids can generally be selected from the group of di-carboxylic acids, in which the aliphatic acid residues are biocompatible aliphatic, saturated or unsaturated di-carboxylic acids, such as succinic acid, fumaric acid, malic acid, malonic acid, glutaric acid, 2-oxoglutaric acid, or longer chain di-carboxylic acids such as sebacic acid. For diesters derived from mono-alcohols, the mono-alcohols for use with short dicarboxylic acids (such as succinic acid, fumaric acid, malic acid, malonic acid, glutaric acid, 2-oxoglutaric acid) are selected from the group of biocompatible monohydroxy alcohols of 10-carbons or longer, with particular attention to capryl alcohol and oleyl alcohol as forming esters with adequately low melting points but also adequately low tissue irritative qualities and acceptable odor. This generally requires esters with a total carbon number of 16 or more. Preferred examples of such liquid diesters based on di-acids and mono-alcohols are dioleyl fumarate, dioleyl malonate, and di-propyl sebacate. Mixed esters such as capryl oleyl succinate are also suitable.

The biocompatible triesters can be composed of residues of biocompatible tri-alcohols, such as glycerol, and mono-acids. Alternatively, triesters can also be made from the esters of biocompatible tricarboxylic acids, such as citric and isocitric acid, and monoalcohols. Preferred tri-alcohol triesters include the liquid natural triglycerides, and other synthetic triglycerides. These triglycerides include, but are not restricted to, glycerol trioleate, medium chain triglyceride oil, and mixed glyceride esters, in which acyl groups derived from caprylic and oleic acid are preferred. The corresponding liquid triesters derived from tricarboxylic acid esters and monoalcohols include, but are not restricted to, tricapryl citrate, trioleyl citrate, tricapryl isocitrate, trioleyl isocitrate, and mixed alcohol esters of citric and isocitric acid.

Lastly, water-immiscible biocompatible solvents for use in the present invention can also be selected from the group of benzoic acid esters of ethanol, n-propanol, isopropanol, and benzyl alcohol. Also, oleic acid may be used directly as a solvent.

Depending upon the specific water immiscible solvent selected for use in preparing the anesthetic solution, propofol concentrations of up to 10% by weight of propofol to the volume of the microemulsion preparation are attainable. In this regard, however, due to the relatively low viscosities of the PEG-containing surfactant Solutol® and the solvent ethyl oleate, these substances are most preferred in that their utilization produces an anesthetic microemulsion containing the highest concentration of propofol of 10% by weight of propofol to the volume of the microemulsion liquid. Again, such an anesthetic is a transparent propofol microemulsion, having a very faint opalescence. When further diluted to 6% weight propofol/volume of total liquid, this microemulsion will exhibit excellent optical clarity.

It will be apparent to those skilled in the art that in addition to the solvents described above, any of the solvents can be mixed with any of the other solvents without deviating from the scope of the present invention.

EXAMPLES

Example #1

Propofol 1% (Weight/Volume=w/v) Microemulsion in Saline using PEG-23 Monostearate Alone One gram of PEG-23 monostearate is heated in a 20 mL glass bottle enough to melt the surfactant, after which it is mixed with 100 mg of propofol. Before this mixture can solidify, 9 mL of warm physiologic saline (0.9% w/v sodium chloride in water, hereafter referred to as "saline") is mixed in to give a final microemulsion containing 1% propofol by weight. This emulsion is optically transparent (with some minor opalescence), and colored very pale yellow from the propofol. This solution is comparable to the commercial 1% propofol product, but contains no soy or egg products to support microbial growth.

Example #2

Propofol 4% (w/v) Microemulsion in Saline using Solutol HS-15 Alone

To make 4% propofol, 3.2 grams of Solutol HS-15 is melted as previously described, and 400 mg of propofol is added and mixed to form the emulsion base. Then warm saline is slowly mixed into the emulsion base. After addition of 4 mL of saline, a characteristic gel forms, characteristic of the bicontinuous fluid resulting from about equal weights of water and emulsification agent. After a total of 6.4 mL saline is added, a total of 10 mL of freely-flowing optically clear microemulsion of drug in water is obtained, which is 32% by weight Solutol HS-15. Such emulsions and solutions containing about 30% Solutol-HS are of low enough viscosity for intravenous injection without pain, according to the pharmacological literature on Solutol HS-15. The resulting microemulsion contains a concentration of propofol of 4% w/v (4 times the present standard commercial concentration) and is found to be suitable for direct injection intravenously, as are all of the Solutol HS-15 based microemulsions described below.

Example #3

Anesthesia of a Dog with Microemulsion Prepared in Example #2

A 30.5 kg animal had been pre-treated with 25 mg acepromazine and 0.2 mg atropine. He was conscious with eyes open, but sedated when injected with 3 ml (120 mg propofol=about 4 mg/kg) of the 4% propofol solution from example #2, directly into a foreleg vein. Within 30 seconds the dog was fully relaxed and was rapidly assessed at level 3, plane 2 anesthesia, with no blink reflex, inability to hold jaw closed, and no gag on endotracheal intubation. Apnea lasted 15 seconds, then spontaneous breathing began. The animal tolerated the endotracheal tube for 35 minutes before opening eyes and beginning gag behavior, necessitating tube removal. The animal was fully recovered within one hour. When the same animal was treated identically on the following day, but without acepromazine or atropine pre-treatment, he showed consciousness and gag at 12 minutes post anesthetic administration. When given intravenously to a fully conscious animal without pretreatment, this microemulsion was observed during injection to cause no effect before unconsciousness, save brief tongue-licking (we believe indicative of the animal tasting the anesthetic). The animal showed no evidence of nausea/vomiting, or IV injection pain.

Example #4

Preparation of Propofol 10% (w/v) Microemulsion in Saline using Solutol HS-15, Ethanol, and Ethyl Oleate as the Hydrophobic Co-Solvent To make 10% propofol microemulsion, 3.0 grams of Solutol HS-15 is melted as previously described, and 1.0 g of propofol, 0.3 g of ethyl oleate, and 0.6 gram of ethanol added and mixed to form the emulsion base. Then warm saline is slowly mixed into the emulsion base. After addition of 5.1 mL of saline, a total of 10 mL of freely-flowing optically clear (but slightly opalescent) microemulsion of drug in water is obtained, which is 30% by weight Solutol HS-15. The described emulsion is 10% by weight propofol (10 times the commercial concentration) and after 0.2 micron filtration is found to be suitable for slow direct injection intravenously.

MCT oil and benzyl acetate at the same weight as ethyl oleate may replace ethyl oleate in this 10% preparation, although for these co-solvents an equal weight ratio of ethanol to propofol must typically be used, for the highest concentrations of propofol such as 10% w/v. Thus, 3.0 grams of Solutol, 1.0 gram of propofol, 1.0 gram of ethanol, 0.3 gram of MCT and 4.7 gram of saline would be used in the mixture above, to obtain a 10% propofol microemulsion using MCT.

Example #5

Anesthesia of a Dog with 10% w/v Microemulsion Prepared as in Example #4 using Ethyl Oleate A 23.3 kg animal was not pretreated. He was injected with 1.5 ml (150 mg propofol =about 6 mg/kg) of the 10% propofol solution from example #4, directly into a foreleg vein. Within 30 seconds the dog relaxed and was rapidly assessed at level 3, plane 2 anesthesia, with no blink reflex, inability to hold jaw closed, and no gag on endotracheal intubation. No apnea was noted. The animal tolerated the endotracheal tube for 11 minutes before opening his eyes and beginning gag behavior, necessitating tube removal. The animal lifted his head at 15 minutes after being given anesthesia.

Example #6

Preparation of 5% Propofol w/v Microemulsion in Saline using Solutol HS-15, Ethanol, and Ethyl Oleate as Hydrophobic Co-Solvent To make 5% propofol, 2.5 grams of Solutol HS-15 is melted as previously described and 0.5 g propofol, 0.25 g ethyl oleate, and 0.5 gram ethanol is added and mixed to form the emulsion base. Then, warm (50° C.) saline is slowly mixed into the emulsion base. After addition of 6.25 mL of saline, a total of 10 mL of freely-flowing optically clear microemulsion of 5% drug in water is obtained, which is 25% by weight Solutol HS-15. After sterile filtration this is suitable for injection. This 5% microemulsion was found to maintain excellent optical clarity and stability for more than one year at room temperature.

Example #7

Preparation of 3% (w/v) Propofol Microemulsion in Saline using Solutol HS-15, Ethanol, and Ethyl Oleate as Hydrophobic Co-Solvent To make 3% propofol microemulsion which is suitable for further dilution, with complete clarity and no opalescence, to lower concentrations such as 2% or 1%, the following method is used: 2.4 grams of Solutol HS-15 is melted as previously described, and 0.3 g propofol, 0.15 g ethyl oleate, and 0.3 gram ethanol added and mixed to form the emulsion base. Then, warm (50° C.) saline is slowly mixed into the emulsion base. After addition of 6.85 mL of saline, a total of 10 mL of freely-flowing optically clear microemulsion of 3% drug in saline is obtained, which is 24% by weight Solutol HS-15. After sterile filtration this is suitable for injection. Further dilutions to 2% or 1% drug (w/v), as is used below, may be made by simple addition of physiologic saline to this microemulsion.

Example #8

Anesthesia of a Dog with 1% (w/v) Propofol Microemulsion, Prepared as in Example #7 using MCT in Place of Ethyl Oleate, then Diluted with Saline To make lower concentrations of propofol, one part of the microemulsion of Example #4 or the equivalent made with MCT in place of ethyl oleate, may be appropriately diluted with 3 parts saline to a final propofol concentration of 1%. Microemulsions of greater than 4% propofol typically exhibit brief cloudiness on addition of saline, which resolves and again becomes transparently opalescent on mixing. Properly constructed microemulsions of less than 3% propofol as in Example #7, which have a higher ratio of Solutol to propofol, typically remain completely optically transparent after dilution and mixing.

Such microemulsions are stable to the eye, with or without refrigeration, for at least 8 weeks. Such a 1% propofol microemulsion was made as in Example #4 but replacing ethyl oleate with MCT, and finally diluted to 1% propofol content with saline. A 15.4 kg dog pre-treated with 15 mg acepromazine and 0.2 mg atropine exhibited a 15 minute span between anesthesia and gag reflex return, after being given 70 mg (7 mL=about 3 mg/mL) of this 1% propofol preparation by I.V. This is indistinguishable to doses of propofol anesthetic needed, and typical response to them, when commercially available 1% propofol preparations are used in dogs.

Example #9

Preparation of Liquid Anhydrous Microemulsion Base Containing Propofol 13.3% (w/v), using Solutol HS-15, Ethanol, and Ethyl Oleate as Hydrophobic Co-Solvent To make 13.3% propofol liquid microemulsion base suitable for reconstituting 5% propofol microemulsion at room temperature with saline, 80.0 grams of Solutol HS-15 is melted as previously described, and 16.0 g propofol, 8.0 g ethyl oleate, and 16.0 grams ethanol is added and mixed to form the microemulsion base. The base may then be filtered and stored at room temperature in a brown glass vial, under air or vacuum. For reconstitution, a suitable amount of microemulsion base is withdrawn from the vial with a syringe and needle, and reconstituted with room-temperature sterile physiologic saline-for-injection. A ratio of 8 parts saline to 3 parts liquid base is used, gently agitating the mixture for 1 to 2 minutes in the syringe or a second vial, at room temperature. The resulting 5% wt/v microemulsion preparation of propofol is suitable for intravenous injection after about 5 minutes of spontaneous de-bubbling.

Although the present invention has been described in its preferred embodiment and in certain other embodiments, it will be recognized by those skilled in the art that other embodiments and features may be provided without departing from the scope of the invention, which is defined by the appended claims.

We claim:

1. A self-microemulsifiable anhydrous base composition for use in the preparation of a spontaneously formed and thermodynamically stable microemulsion that can be used as an anesthetic composition, comprising:
   a) liquid propofol;
   b) a nonionic surfactant consisting of polyoxyethylene (POE) having the structure of [POE(n)] subm-R'-R; where POE (n) is a polyoxyethylene moiety of -mer number n, and having m of these POE functional groups attached to R'; where the value of m is one to three; where R' is a linking moiety selected from glyceryl, sorbitan, ester, amino, or ether functions; where R is a hydrophobic moiety consisting of saturated or unsaturated alkyl or alkylphenyl groups; and where the structure of the nonionic surfactant is further defined by a ratio of A, the total number of POE -mer units in the surfactant given by the product of -mer number n and total POE chain number m per molecule, to B, the number of carbons in the hydrophobic functional group R, the ratio of A/B being in the range of about 0.7 to 4, with the base composition not containing any other surfactant other than said nonionic surfactant having said structure;
   c) a water-immiscible solvent which is selected from the group consisting of a biocompatible monoester, diester and triester;
   d) ethanol; and
   wherein the relative concentration of the nonionic surfactant to propofol included in the base composition is not less than about three (3) parts of the nonionic surfactant to about one (1) part propofol, the relative concentration of the water-immiscible solvent to propofol is about three (3) to five (5) parts solvent to about ten (10) parts propofol, and the relative concentration of ethanol to propofol is about five (5) to six (6) parts ethanol to about ten (10) parts propofol.

2. The base composition of claim 1 in which the nonionic surfactant is selected from the group consisting of polyoxyethylene monoalkyl ethers, polyoxyethylene alkylphenols, polyethylene glycol fatty acid monoesters, polyethylene glycol glycerol fatty acid esters, polyoxyethylene sorbitan fatty acid esters, and polyoxyethylene sterols.

3. The base composition of claim 1 in which the nonionic surfactant is selected from the group consisting of PEG-15 monolaurate, PEG-20 monolaurate, PEG-32 monolaurate, PEG-48 monolaurate, PEG-13 monooleate, PEG-15 monooleate, PEG-20 monooleate, PEG-32 monooleate, PEG-72 monooleate, PEG-15 monostearate, PEG-660 12-hydroxystearate, PEG-23 monostearate, PEG-40 monostearate, PEG-72 monostearate, PEG-20 glyceryl laurate, PEG-30 glyceryl laurate, PEG-20 glyceryl stearate, PEG-20 glyceryl oleate, PEG-30 glyceryl monooleate, PEG-30 glyceryl monolaurate, PEG-40 glyceryl monolaurate, PEG-20 sorbitan monooleate, PEG-20 sorbitan monolaurate, PEG-20 sorbitan monopalmitate, and PEG 20 sorbitan stearate, PEG-40 sorbitan monooleate, PEG-80 sorbitan monolaurate, POE-23 lauryl ether, POE-20 oleyl ether, PEG-30-60 nonyl phenol series, PEG-30-55 octyl phenol series, and mixtures thereof.

4. The base composition of claim 1 in which the base composition is homogeneous.

5. The base composition of claim 1 in which the base composition is optically transparent.

6. The base composition as in claim 1 in which the monoester is selected from the group consisting of ethyl oleate, isopropyl myristate, ethyl laurate, butyl oleate, oleyl acetate, oleyl propionate, octyl octanoate, octyl decanonate, and oleyl oleate.

7. The base composition as in claim 1 in which the water-immiscible solvent is a diester derived from a di-alcohol and a mono-acid.

8. The base composition as in claim 7 in which the diester is selected from the group consisting of propylene glycol dilaurate, propylene glycol dioleate, propylene glycol dicaprylate and 1, 2 butane glycol dioleate.

9. The base composition as in claim 1 in which the water-immiscible solvent is a diester derived from a di-acid and a mono-alcohol.

10. The base composition as in claim 9 in which the diester is selected from the group consisting of dioleyl succinate, diethyl fumarate, diethyl malate, and diethyl adipate.

11. The base composition as in claim 1 in which the water-immiscible solvent is a triester derived from an aliphatic acid and a trialcohol.

12. The base composition as in claim 11 in which the triester is a triglyceride.

13. The base composition as in claim 12 in which the triglyceride is selected from the group consisting of glycerol tri-oleate and a medium chain triglyceride oil.

14. The base composition as in claim 1 in which the water-immiscible solvent is a triester derived from an aliphatic tri-carboxylic acid and a mono-alcohol.

15. The base composition as in claim 14 in which the triester is selected from the group consisting of a triethyl citrate, tributyl citrate, or triethyl isocitrate.

16. The base composition as in claim 1 in which the water-immiscible solvent is selected from the group consisting of benzoic acid esters of ethanol, n-propanol, isopropanol, and benzyl alcohol.

17. The base composition of claim 1 that further comprises a physiologic carrier liquid that is isotonic to blood, thereby forming the microemulsion.

18. The microemulsion of claim 17 in which the microemulsion is optically transparent.

19. The microemulsion of claim 17 in which the concentration of the propofol is included in the microemulsion in an amount of up to about 5% by weight of the propofol to the volume of the microemulsion.

20. The microemulsion of claim 17 in which the concentration of the propofol is included in the microemulsion in an amount of up to about 10% by weight of the propofol to the volume of the microemulsion.

21. A method of preparing the self-microemulsifiable base composition as in claim 1, comprising the steps of:
   a) measuring about five parts of the nonionic surfactant to about one part of propofol and heating said nonionic surfactant to a preparation temperature above its melting point; and
   b) combining the nonionic surfactant with predetermined amounts of water-immiscible solvent, ethanol and propofol; thereby forming the base composition.

* * * * *